United States Patent
Back

(10) Patent No.: US 9,255,016 B2
(45) Date of Patent: Feb. 9, 2016

(54) MULTIPLE SEPARATION FILTER AND ANTIOXIDIZING WATER PRODUCED USING THE SAME

(75) Inventor: Kwang Sung Back, Seoul (KR)

(73) Assignee: LS NOVA CO., LTD., Matsudo-shi (JP)

(*) Notice: Subject to any disclaimer, the term of this patent is extended or adjusted under 35 U.S.C. 154(b) by 77 days.

(21) Appl. No.: 14/236,897

(22) PCT Filed: Jun. 1, 2012

(86) PCT No.: PCT/KR2012/004358
§ 371 (c)(1),
(2), (4) Date: Feb. 3, 2014

(87) PCT Pub. No.: WO2013/018989
PCT Pub. Date: Feb. 7, 2013

(65) Prior Publication Data
US 2014/0178491 A1    Jun. 26, 2014

(30) Foreign Application Priority Data

Aug. 4, 2011    (KR) .......................... 10-2011-0077804

(51) Int. Cl.
*C02F 1/44* (2006.01)
*B01D 39/14* (2006.01)
*C02F 1/28* (2006.01)
(Continued)

(52) U.S. Cl.
CPC ................. *C02F 1/444* (2013.01); *A61K 33/00* (2013.01); *B01D 39/14* (2013.01); *B01D 71/32* (2013.01); *C02F 1/001* (2013.01); *C02F 1/281* (2013.01); *B01D 67/0009* (2013.01); *C02F 1/283* (2013.01); *C02F 1/44* (2013.01); *C02F 1/70* (2013.01); *C02F 2001/46195* (2013.01)

(58) Field of Classification Search
None
See application file for complete search history.

(56) References Cited

U.S. PATENT DOCUMENTS

2007/0199582 A1* 8/2007 Kroon .................. B67D 1/0009
134/56 R
2008/0302713 A1* 12/2008 Patrick .................. B01D 65/08
210/234

FOREIGN PATENT DOCUMENTS

| JP | 01-306510 A | 12/1989 |
| JP | 10-118653 A | 5/1998 |

(Continued)

OTHER PUBLICATIONS

Machine Translation for JP 2005 040765 A, Murota et al., Feb. 17, 2005.*

(Continued)

*Primary Examiner* — Carlos Azpuru
*Assistant Examiner* — Casey Hagopian
(74) *Attorney, Agent, or Firm* — Christensen O'Connor Johnson Kindness PLLC

(57) ABSTRACT

Disclosed is a multiple separation filter including a microfiltration membrane, an active carbon-based filter and a ceramic filter stacked in order, wherein the active carbon-based filter is obtained by mixing active carbon with at least one selected from zeolite, gold, silver and a mixture thereof, treating the mixture with plasma gas of 60,000° C. to 70,000° C., and then quenching the mixture to −200° C. to −273° C. under vacuum, and the ceramic filter is obtained by quenching plasma gas generated by heating magnesium at 60,000° C. to 70,000° C. to −200° C. to −273° C. under vacuum. Disclosed also is antioxidant water obtained by using the multiple separation filter. The antioxidant water has a negative oxidation reduction potential.

4 Claims, 1 Drawing Sheet

(51) Int. Cl.

| | | |
|---|---|---|
| *C02F 1/00* | (2006.01) | |
| *C02F 1/70* | (2006.01) | |
| *C02F 1/461* | (2006.01) | |
| *A61K 33/00* | (2006.01) | |
| *B01D 67/00* | (2006.01) | |
| *B01D 71/32* | (2006.01) | |

(56) References Cited

FOREIGN PATENT DOCUMENTS

| | | | |
|---|---|---|---|
| JP | 2005040765 A | * | 2/2005 |
| JP | 2010-14466 A | | 1/2010 |
| KR | 10 2000 0066370 A | | 10/2002 |
| KR | 10-0437990 B1 | | 6/2004 |
| KR | 10-2004-0039907 A | | 12/2004 |

OTHER PUBLICATIONS

International Search Report mailed Dec. 26, 2012, issued in corresponding International Application No. PCT/KR2012/004358, filed Jun. 1, 2012, 2 pages.

Li, W-H, et al., "Thermal Contraction of Au Nanoparticles," Physical Review Letters (89)13:1-4, Sep. 23, 2002.

Shigeta, M., DSpace Software Copyright © 2002-2006 MIT and Hewlett Packard, Kyoto University Information Repository, pp. 165-171, Feb. 2007.

Yamamoto, Y., et al., "X-Ray Magnetic Circular Dichroism Study of Gold Nanoparticles Protected by Polimer," Journal of Magnetism and Magnetic Materials 272-276:1183-1184, 2004.

* cited by examiner

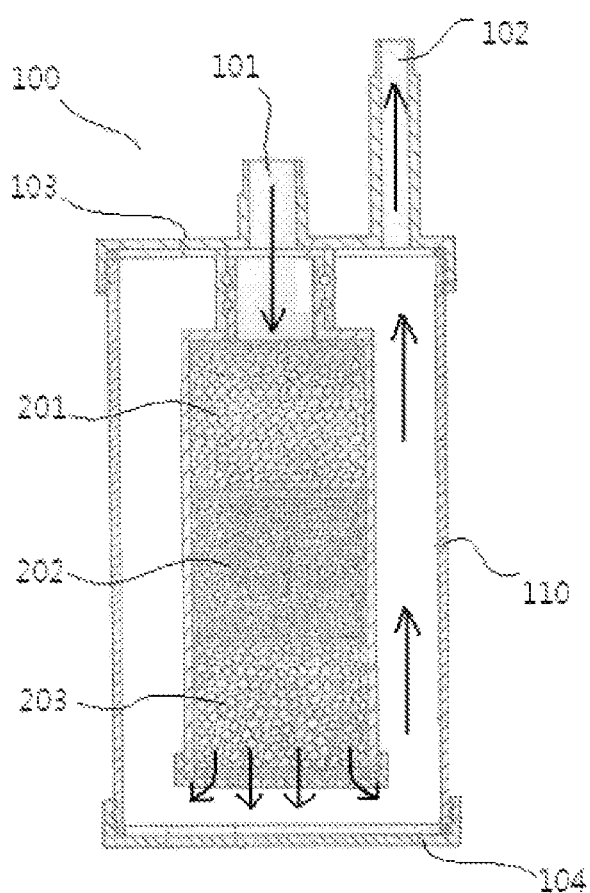

MULTIPLE SEPARATION FILTER AND ANTIOXIDIZING WATER PRODUCED USING THE SAME

TECHNICAL FIELD

The present invention relates to a multiple separation filter including a microfiltration membrane, zeolite, active carbon and ceramics, a method for producing the filter, and antioxidant water produced by using the filter.

BACKGROUND ART

As an income level and standard of living are improved, purified water with better quality as general water for living is increasingly in demand. In addition, with regard to drinking water, use of high-quality functional water such as ionized water, alkaline reduced water or soft water is increasingly in demand. Under these circumstances, functional products having various functionalities imparted to conventional filter structures, such as a water softener, water ionizer, system for producing alkaline reduced water and a bidet, have been developed actively.

In general, it is recognized that alkaline reduced water that has been subjected to electrolysis sufficiently is effective for treating abnormal fermentation in the stomach, chronic diarrhea, indigestion, hyperacidity and constipation, and thus most systems for ionizing water to produce electrolyzed alkaline water are thought as medical production systems rather than water purifiers. In addition, such alkaline water forms a part of health aid agents as antioxidant water.

In this context, commercially available systems for producing antioxidant water are those for producing alkaline antioxidant water through the electrolysis of water using galvanism. However, since such electrolysis systems are very expensive, many approaches using various mineral-based ceramics have been suggested.

With regard to a system for producing alkaline antioxidant water using mineral substances such as ceramics, Korean Laid-Open Patent No. 10-2007-0007979 discloses a multi-layer filter having filter layers including various ingredients and stacked in order. Herein, such a multi-layer filter for producing alkaline antioxidant water includes a first hydrogen reduction filter layer having anion-generating layers of beads, pH-adjusting layers of beads, reduction catalyst layers, and secondary hydrogen reduction filter having anion-generating alkaline layers of beads layer.

Particularly, the antioxidant water produced and commercialized by the methods according to the related art is also called electrolyzed reduced water or hydrogen-enriched water, when it is obtained by electrolysis of water. However, since hydrogen molecules contained in such electrolyzed reduced water are scattered in the air gradually with time, resulting in a decrease in amount of hydrogen, such water cannot function as antioxidant water. In addition, the system for producing electrolyzed reduced water is expensive in itself and requires high holding cost.

On the other hand, there is a commercialized product having a hydrogen-generating mineral stick attached to a water container and developed in a simple and cost-efficient manner. Such a product allows production and intake of reduced water as desired and is highly cost-efficient. However, in this case, there still exists the above-mentioned problem of a rapid decrease in hydrogen content in antioxidant water with time. Moreover, the hydrogen-generating mineral stick has no water-purifying function, and thus can be used merely in the case of purified water.

DISCLOSURE

Technical Problem

A technical problem to be solved by the present invention is to provide a multiple separation filter for producing antioxidant water that resolves the above-mentioned problem, and particularly maintains a stable proton concentration in water with time goes and maintains alkaline property even after the lapse of time.

Technical Solution

In one general aspect, there is provided a multiple separation filter for water treatment having at least three membranes or filters stacked in order. More particularly, the multiple separation filter includes a microfiltration membrane, an active carbon-based filter and a ceramic filter.

Particularly, according to an embodiment, the multiple separation filter includes a microfiltration membrane, an active carbon-based filter and a ceramic filter stacked in order, wherein the active carbon-based filter is obtained by mixing 60 parts by weight of active carbon with 20-40 parts by weight of zeolite powder, treating the mixture with plasma gas of 60,000° C. to 70,000° C., and then quenching the mixture to −200° C. to −273° C. under vacuum, and the ceramic filter is obtained by heating magnesium using plasma gas of 60,000° C. to 70,000° C., and quenching it to −200° C. to −273° C. under vacuum.

According to another embodiment, the multiple separation filter includes a microfiltration membrane, an active carbon-based filter and a ceramic filter stacked in order, wherein the active carbon-based filter is obtained by mixing 60 parts by weight of active carbon with 20-40 parts by weight of at least one powder selected from gold and silver, treating the mixture with plasma gas of 60,000° C. to 70,000° C., and then quenching the mixture to −200° C. to −273° C. under vacuum, and the ceramic filter is obtained by heating magnesium by using plasma gas of 60,000° C. to 70,000° C., and then quenching it to −200° C. to −273° C. under vacuum.

According to still another embodiment, the multiple separation filter includes a microfiltration membrane using a polymer membrane obtained by HTIPS (hydrothermally induced phase separation) of PVDF (polyvinylidene fluoride), polyethylene, polypropylene, polystyrene, polyisobutylene, polyvinyl chloride, Teflon, polyacrylonitrile, polymethyl methacrylate, nylon, bakelite, urea resins, polysiloxane, or a mixture thereof.

According to yet another embodiment, the microfiltration membrane has pores distributed uniformly therein, wherein the pores have a diameter of 0.025-10 μm, and/or the microfiltration membrane has a porosity of 60%-70%.

In another general aspect, there is provided antioxidant water obtained by using a multiple separation filter. According to an embodiment, the antioxidant water has an oxidation reduction potential of −729 mV to −94 mV, and is obtained by using a multiple separation filter including a microfiltration membrane, an active carbon-based filter and a ceramic filter stacked in order, wherein the active carbon-based filter is obtained by mixing 60 parts by weight of active carbon with 20-40 parts by weight of powder of zeolite, gold, silver or a mixture thereof, treating the mixture with plasma gas of 60,000° C. to 70,000° C., and then quenching the mixture to −200° C. to −273° C. under vacuum; and the ceramic filter is obtained by u heating magnesium using plasma gas of 60,000° C. to 70,000° C. to −200° C., and then quenching it to −273° C. under vacuum.

According to another embodiment, the antioxidant water has an oxidation reduction potential of −729 mV to −94 mV, and is obtained by using a multiple separation filter including a microfiltration membrane, an active carbon-based filter and a ceramic filter stacked in order, wherein the active carbon-based filter is obtained by mixing 60 parts by weight of active carbon with 20-40 parts by weight of powder of zeolite, gold, silver or a mixture thereof, treating the mixture with plasma gas of 60,000° C. to 70,000° C., and then quenching the mixture to −200° C. to −273° C. under vacuum; the ceramic filter is obtained by quenching plasma gas generated by heating magnesium using plasma gas of 60,000° C. to 70,000° C., and quenching it to −200° C. to −273° C. under vacuum; and the microfiltration membrane uses a polymer membrane obtained by HTIPS (hydrothermally induced phase separation) of PVDF (polyvinylidene fluoride), polyethylene, polypropylene, polystyrene, polyisobutylene, polyvinyl chloride, Teflon, polyacrylonitrile, polymethyl methacrylate, nylon, bakelite, urea resins, polysiloxane, or a mixture thereof.

Advantageous Effects

The antioxidant water according to the present invention has reducing property, makes water clusters smaller so that water has the same clusters as intracellular water of healthy humans, and can be used as drinking water having strong antioxidant power capable of removing active oxygen in the human body. The drinking water obtained according to the present invention is antioxidant water having excellent reducing power and functions to remove active oxygen in vivo.

When the antioxidant water according to the present invention is used as drinking water, it has small water clusters to provide high intracellular absorptivity, clarifies blood and body fluids, and enhances in vivo immunity level.

DESCRIPTION OF DRAWINGS

FIG. 1 is a schematic view illustrating a non-limiting example of a system for producing antioxidant water equipped with a multiple separation filter according to the present invention.

DETAILED DESCRIPTION OF MAIN ELEMENTS

100: system for producing antioxidant water
101: crude water inlet
102: antioxidant water outlet
103: upper cap
104: lower cap
110: housing
201-203: multiple separation filters

BEST MODE

Microfiltration Filter

The multiple separation filter according to the present invention includes a microfiltration membrane.

In the field of water treatment, membrane separation processes may be classified broadly into those based on microfiltration (MF), ultrafiltration (UF), nanofiltration (NF) and reverse osmosis (RO). A microfiltration process is referred to as a process for separating particles with a colloidal size or more not dissolved in solution, and the separation membrane used therefor is referred to as a microfiltration membrane.

A microfiltration membrane should have a uniform pore size, high porosity and a small thickness of its active layer in which at least pores allowing substantial separation are present, so that it functions effectively.

The microfiltration membrane according to the present invention is differentiated from the other membranes or filters by its pore size, and is a separation membrane having pores with a diameter of 0.025-10 µm, preferably 0.025-1 µm, and more preferably 0.025-3 µm. A microfiltration membrane should have controlled porosity in such a manner that there is no interruption even when a large-size solute dissolved in solution passes through the membrane, and thus has a porosity of 60%-70% in general.

The microfiltration membrane is preferably used for the preparation of edible water, and can be regenerated and reused several times or used only once. On the other hand, the microfiltration membrane may be used for sterilization, and thus applied to pharmaceuticals or medicines. In other words, since small bacteria have a size of about 0.3 µm, most bacteria can be removed by the microfiltration membrane according to the present invention for medical application. In addition, colloidal microparticles can be removed by the sieving mechanism of a microfiltration membrane.

Various types of microfiltration membranes have been developed and commercialized to date. In the early stage of the development of microfiltration membranes, most microfiltration membranes were based on nitrate. However, due to the safety problem in manufacturing processes, microfiltration membranes using various materials, such as polyamide, polysulfone, polyvinylidene fluoride, polypropylene, cellulose acetate, polyethylene, polytetrafluoroethylene or polyethersulfone, have been commercialized recently.

The microfiltration membrane according to the present invention is based on a polymeric material such as PVDF (polyvinylidene fluoride), and is obtained by a hydrothermally induced phase separation process (HTIPS) in the form of a membrane. In other words, at a temperature above the melting point of a polymer, the polymer is melt blended with a diluent capable of dispersing the polymer finely to form a homogeneous single-phase molten solution, which, in turn, is formed into an adequate membrane shape. Then, the added hydrothermal heat is quenched to cause phase separation, and the diluent is extracted with a suitable extracting agent, thereby leaving voids in the polymer matrix so that the polymer matrix is provided with porosity as a whole. Herein, it is possible to control the size of a phase separation domain and pore size by adjusting the quenching rate.

The microstructure of a polymer matrix, polymer membrane, obtained by the HTIPS process depends on the types of polymer and diluent used therefor and the phase separation process. Thus, it is possible to change the size and shape of pores while maintaining a uniform pore size distribution by controlling the above parameters adequately, so that the polymer membrane may be used as a multi-purpose membrane. In addition, it is possible to extend the spectrum of materials to crystalline polymers and high-strength engineering plastics. According to the present invention, in addition to PVDF, polymer materials such as polyethylene, polypropylene, polystyrene, polyisobutylene, polyvinyl chloride, Teflon, polyacrylonitrile, polymethyl methacrylate, nylon, bakelite, urea resins, polysiloxane or a mixture thereof may be formed into a microfiltration membrane through a hydrothermally induced phase separation process.

Active Carbon-Based Filter

The microfiltration filter according to the present invention includes an active carbon-based filter, which uses active carbon as a main ingredient and contains zeolite, magnesium, gold, silver or a mixture thereof incorporated thereto.

Active carbon is formed of carbon aggregate having innumerable pores (micropores, mesopores, and macropores) and is known widely as adsorbent for purifying air, gas or liquid. The active carbon-based filter according to the present invention is a filter that includes active carbon as a main ingredient to which zeolite or magnesium is added or applied.

As used herein, active carbon is provided preferably as granules, spheres, clusters or powder, and any types of active carbon may be used as long as they have internal pores at the molecular level and a network structure. Preferably, active carbon has an internal surface area of 500-1,500 $m^2/g$ or more.

Herein, carbides activated by various methods may be used. It is preferred to use carbides obtained by a gas process in which fixed carbon is oxidized with water vapor or carbon dioxide at a high temperature of 800-900° C., or by a chemical treatment process in which carbide is treated chemically and micropores are extended by using sulfuric acid, phosphoric acid or zinc chloride. The activation of carbide is carried out by either the gas process or the chemical activation process. Particularly, it is possible to use an in-situ gas activation process in which carbide is oxidized partially with oxidative gas such as water vapor, carbon dioxide, oxygen or air at a temperature of about 900° C. to generate micropores in situ, because no solid is discharged except active carbon. In addition, although the activating agent is mixed with active carbon and thus an additional washing step is required, it is preferred to use a chemical activation process in which a carbide or non-carbide material is activated via chemical reaction with an activating agent such as zinc chloride, phosphoric acid, potassium hydroxide or sodium hydroxide.

In a variant, it is preferred to use powdery active carbon or particulate active carbon as active carbon. Preferably, powdery active carbon is obtained by heating dry sawdust to 300-500° C. to perform carbonization while preventing oxidation, thereby forming calcined ashes, and then activating the calcined ashes in an activation furnace maintained at 800-1000° C. In addition, particulate active carbon is obtained preferably by activating palm shells obtained through the incomplete combustion of palm skins in a kiln at 800-1000° C., followed by pulverization into a size up to 8-30 mesh.

As used herein, zeolite is an ingredient incorporated to the active carbon-based filter and is a generic name of crystalline aluminosilicates. Since zeolite has a negative charge at any site of aluminum in aluminosilicate, cations are present in the pores for the purpose of charge offset. In addition, the remaining space in the pores is filled with water molecules in general. The three-dimensional pore structure of zeolite varies with its shape and size. However, it is preferred that the zeolite according to the present invention includes pores having a diameter at the molecular level. Herein, it is possible to control the size selectivity and shape selectivity to the molecules accepted by the pores of zeolite, and thus zeolite functions as a molecular sieve.

No ion exchanging agent has been known for removing harmful cationic and anionic compounds, including heavy metal ions, present in wastewater and water effectively at the same time. In general, an ion exchanging agent having activity toward the removal of cations and another ion exchanging agent having activity toward the removal of anions are simply mixed physically in order to remove the harmful cations and anions present in water at the same time. However, the active carbon-based filter according to the present invention uses zeolite, magnesium, gold, silver, etc., in combination, and thus can remove not only microbial contaminants, such as bacteria or germs, but also harmful cations and anions at the same time.

As used herein, the term 'zeolite' covers zeolite, including a pseudo-molecular sieve, in a broad sense. In other words, zeolite applicable to the present invention is a molecular sieve, and particular non-limiting examples thereof include natural and synthetic zeolites, pseudo-molecular sieves in which the silicon atoms of the zeolite backbone are partially or totally substituted with another atom such as phosphorus (P) (e.g. $AlPO_4$, SAPO, MeAPO, MeAPSO), molecular sieves in which the aluminum atoms of the zeolite backbone are partially or totally substituted with another atom such as boron (B), gallium (Ga) or titanium (Ti), molecular sieves obtained by any combination of the above, molecular sieves of porous metals or silicon oxide (e.g. silicalite, MOM-based porous silica, porous titanium dioxide, niobium dioxide, or the like) and composite oxides thereof, and porous molecular sieves obtained by using other different elements alone or in combination.

As used herein, zeolite includes, but is not limited to: analcime (hydrated sodium aluminosilicate), pollucite (hydrated cesium sodium aluminosilicate), wairakite (hydrated calcium sodium aluminosilicate), bellbergite (hydrated potassium barium strontium sodium aluminosilicate), bikitaite (hydrated lithium aluminosilicate), boggsite (hydrated calcium sodium aluminosilicate), brewsterite (hydrated strontium barium sodium calcium aluminosilicate), chabazite (hydrated calcium aluminosilicate) and willhendersonite (hydrated potassium calcium aluminosilicate), cowlesite (hydrated calcium aluminosilicate), dachiardite (hydrated calcium sodium potassium aluminosilicate), edingtonite (hydrated barium calcium aluminosilicate), epistilbite (hydrated calcium aluminosilicate), erionite (hydrated sodium potassium calcium aluminosilicate), faujasite (hydrated sodium calcium magnesium aluminosilicate), ferrierite (hydrated sodium potassium magnesium calcium aluminosilicate), amicite (hydrated potassium sodium aluminosilicate), garronite (hydrated calcium aluminosilicate), gismondine (hydrated barium calcium aluminosilicate) and gobbinsite (hydrated sodium potassium calcium aluminosilicate), gmelinite (hydrated sodium calcium aluminosilicate), gonnardite (hydrated sodium calcium aluminosilicate), goosecreekite (hydrated calcium aluminosilicate), harmotome (hydrated barium potassium aluminosilicate), phillipsite (hydrated potassium sodium calcium aluminosilicate), wellsite (hydrated barium calcium potassium aluminosilicate), clinoptilolite (hydrated sodium potassium calcium aluminosilicate), heulandite (hydrated sodium calcium aluminosilicate), laumontite (hydrated calcium aluminosilicate), levyne (hydrated calcium sodium potassium aluminosilicate), mazzite (hydrated potassium sodium magnesium calcium aluminosilicate), merlinoite (hydrated potassium sodium calcium barium aluminosilicate), montesommaite (hydrated potassium sodium aluminosilicate), mordenite (hydrated potassium calcium aluminosilicate), mesolite (hydrated sodium calcium aluminosilicate), natrolite (hydrated sodium aluminosilicate) and scolecite (hydrated calcium aluminosilicate), offretite (hydrated calcium potassium magnesium aluminosilicate), paranatrolite (hydrated sodium aluminosilicate), paulingite (hydrated potassium calcium sodium barium aluminosilicate), perlialite (hydrated potassium sodium calcium strontium aluminosilicate), barrerite (hydrated sodium potassium calcium aluminosilicate), stilbite (hydrated sodium calcium aluminosilicate) and stellerite (hydrated calcium aluminosilicate), thomsonite (hydrated sodium calcium aluminosilicate), tschernichite (hydrated calcium aluminosilicate), yugawaralite (hydrated calcium aluminosilicate), or a mixture thereof.

In addition, according to the present invention, magnesium, gold or silver metal is incorporated to the active carbon-based filter. Magnesium may be used in the form of silicate, sulfate or carbonate of magnesium. Although magnesium is not present as a single element in its natural state, pure magnesium may be used. Preferably, magnesium is used as powder having a particle diameter of 0.01-0.09 μm. Further, gold or silver is used in the form of powder preferably having a particle diameter of 2-20 nm.

Hereinafter, a method for incorporating zeolite, magnesium, gold or silver to active carbon will be explained.

The active carbon-based filter according to the present invention is obtained by mixing 20-40 parts by weight of at least one powder selected from zeolite, magnesium, gold and silver with 60 parts by weight of active carbon. The resultant mixture is treated with plasma gas of 60,000-70,000 generated by a plasma torch system using an RF power amplifier, followed by quenching to −200 to −273° C. under vacuum. It is shown that the resultant active carbon to which at least one powder selected from zeolite, magnesium, gold and silver is incorporated according to the present invention is paramagnetic.

According to an embodiment, the active carbon-based filter including active carbon and zeolite incorporated thereto has the composition as shown in Table 1.

TABLE 1

| Ingredient | Wt % |
|---|---|
| $SiO_2$ | 68.9 |
| $Al_2O_3$ | 12.4 |
| CaO | 2.6 |
| $Fe_2O$ | 1.4 |
| MgO | 0.2 |
| $Na_2O$ | 1.6 |
| $K_2O$ | 2.2 |
| $P_2O$ | 0.1 |

Ceramic Filter

The multiple separation filter according to the present invention includes a ceramic filter.

As used herein, ceramic is a generic name of products using high-purity natural minerals or inorganic compounds prepared from synthetic materials and provided with high functionalities.

Magnesium has 2 electrons in K electron shell, 8 electrons in L electron shell, and 2 electrons in M electron shell. Among the electrons, the outermost two electrons are unstable and can be released easily, thereby providing reducing power. When magnesium reacts with water, one molecule of magnesium reacts with two molecules of water, wherein magnesium hydroxide is produced while magnesium is not liberated. During the process, a part of the electrons released from magnesium is used for forming hydrogen gas and the residual electrons remain in water. Magnesium hydroxide is ionized to form hydroxide groups ($OH^-$). In other words, magnesium is oxidized while water is reduced, which provides reduced water.

Magnesium is not present as a single element in its natural state but is present mostly in the form of salt with silicic acid, sulfuric acid or carbonic acid. The ceramic filter according to the present invention includes magnesium in the form of salt, and preferably includes pure magnesium. Preferably, the ceramic filter according to the present invention essentially includes magnesium and may include other metals, such as Al, Si or Mn as inevitable impurities.

The ceramic filter according to the present invention includes magnesium as a main ingredient. According to an embodiment, the ceramic filter has the composition as shown in Table 2.

TABLE 2

| Ingredient | Wt % |
|---|---|
| Mg | 99.93 |
| Al | 0.0043 |
| Si | 0.018 |
| Mn | 0.014 |
| Fe | 0.0027 |
| Zn | 0.0022 |
| Cu | 0.0005 |
| Ni | 0.0013 |

The ceramic filter according to the present invention is obtained by quenching plasma gas of 60,000-70,000° C., generated by heating magnesium with a plasma torch system using an RF power amplifier, to −200 to −273° C. under vacuum. It is shown that the ceramic filter according to the present invention is paramagnetic.

Multiple Separation Filter

The multiple separation filter according to the present invention is obtained by stacking the microfiltration membrane, active carbon-based filter and ceramic filter in order in a cartridge filter housing.

According to an embodiment, the multiple separation filter is obtained by stacking the microfiltration membrane and active carbon-based filter in order in a cartridge filter housing.

According to another embodiment, the multiple separation filter is obtained by stacking the microfiltration membrane and ceramic filter in order in a cartridge filter housing.

Method for Producing Antioxidant Water

According to the present invention, crude water is allowed to pass through the multiple separation filter, based on the natural principle of conversion of ground water into natural alkaline water through the mineral-enriched bedrock layer, so as to remove contaminants and harmful ingredients in crude water, and then pass through the ceramic filter layer so as to obtain antioxidant water. Hereinafter, the method for producing antioxidant water by using the multiple separation filter according to the present invention will be explained in detail.

According to the present invention, first, crude water is allowed to pass through a membrane or filter selected from the microfiltration membrane, active carbon-based filter and the ceramic filter to remove impurities and to decrease the oxidation reduction potential to −94 mV to −729 mV, and then is allowed to pass through the multiple separation filter including the microfiltration membrane, active carbon-based filter and the ceramic filter stacked in order in a cartridge filter housing to increase hydrogen concentration and to cleave clusters of water molecules finely, thereby providing antioxidant water.

Particularly, since the ceramic filter according to the present invention has a porous structure whose surface includes micropores distributed thereon, water passing through the ceramic filter is absorbed into the ceramic filter rapidly. The ceramic filter is magnetic and a potential difference of about 20 mV is generated between the N pole and S pole. While water is passed through and absorbed into the filter, microcurrent flows, and thus hydrogen gas is emitted from the N pole, thereby providing reducing power to water.

The multiple separation filter according to the present invention may be used for various types of water purifying systems, as long as it is mounted to a cartridge filter housing having an adequate shape with no limitation of sizes, purposes and types of systems or apparatuses, including household water purifiers, industrial water purifiers, or the like. According to an embodiment, a system for producing antioxidant water is shown in FIG. 1, wherein the filter layers shown as reference numbers 201 to 203 correspond to the multiple separation filter according to the present invention.

The antioxidant water filtered through the water purifying system has a negative (−) oxidation reduction potential value and high reducing power, and preferably has an oxidation reduction potential ranging from −729 to −94 mV, more preferably from −150 to −729 mV.

MODE FOR INVENTION

Preparation Example

PVDF is melt blended homogeneously with soybean oil as diluent in a reaction tank by agitation for 360 minutes while maintaining the temperature at 200° C., and subjected to melt spinning and cooling to room temperature to cause coagulation. Then, the product is extracted with n-hexanol, dried to room temperature, and annealed at 120° C. to form a membrane shape, thereby preparing microfiltration membrane 1.

Next, 60 parts by weight of active carbon is mixed with 30 parts by weight of zeolite, and the mixture is heat treated with plasma gas of 60,000-70,000° C., followed by quenching to −273° C. under vacuum, thereby preparing active carbon-based filter 1. Meanwhile, active carbon is mixed with 30 parts by weight of silver powder instead of zeolite to prepare active carbon-based filter 2 in the same manner.

In addition, ceramic filter 1 based on magnesium and having the same composition as shown in Table 2 is prepared.

Example 1

Microfiltration membrane 1 and active carbon-based filter 1 are stacked in order to provide multiple separation filter 1.

Example 2

Microfiltration membrane 1 and active carbon-based filter 2 are stacked in order to provide multiple separation filter 2.

Example 3

Microfiltration membrane 1, active carbon-based filter 1 and ceramic filter 1 are stacked in order to provide multiple separation filter 3.

Example 4

Microfiltration membrane 1, active carbon-based filter 2 and ceramic filter 1 are stacked in order to provide multiple separation filter 4.

Example 5

Each of multiple separation filters 1 to 4 obtained from Example 1 to 4 is mounted to the system for producing antioxidant water as shown in FIG. 1 to produce antioxidant water. The physical properties of the antioxidant water thus produced are determined at room temperature and shown in the following Table 3 with tap water used as control.

TABLE 3

| | Temperature (° C.) | pH | Oxidation Potential (mV) | Dissolved oxygen content (ppm) | Dissolved hydrogen content (ppb) |
| --- | --- | --- | --- | --- | --- |
| Control: tap water | 13.1 | 7.5 | +652 | 10.0 | 2.6-2.6 |
| Example 1 | 12.7 | 9.8 | −94 | 9.4 | 400-450 |
| Example 2 | 13.2 | 10.3 | −247 | 8.6 | 690-720 |
| Example 3 | 13.2 | 10.4 | −494 | 8.2 | 880-900 |
| Example 4 | 13.7 | 10.7 | −729 | 7.2 | 1030-1060 |

The invention claimed is:

1. A multiple separation filter comprising a microfiltration membrane, an active carbon-based filter and a ceramic filter stacked in order,
   wherein the active carbon-based filter is obtained by mixing 60 parts by weight of active carbon with 20-40 parts by weight of zeolite powder, treating the mixture with plasma gas of 60,000° C. to 70,000° C., and then quenching the mixture to −200° C. to −273° C. under vacuum; and
   the ceramic filter is obtained by heating magnesium by plasma gas of 60,000° C. to 70,000° C., and quenching the magnesium to −200° C. to −273° C. under vacuum.

2. The multiple separation filter according to claim 1, wherein the microfiltration membrane is a polymer membrane obtained by HTIPS (hydrothermally induced phase separation) of PVDF (polyvinylidene fluoride), polyethylene, polypropylene, polystyrene, polyisobutylene, polyvinyl chloride, Teflon, polyacrylonitrile, polymethyl methacrylate, nylon, bakelite, urea resins, polysiloxane, or a mixture thereof.

3. The multiple separation filter according to claim 1, wherein the microfiltration membrane has pores distributed uniformly therein, and the pores have a diameter of 0.025-10 µm.

4. The multiple separation filter according to claim 1, wherein the microfiltration membrane has a porosity of 60%-70%.

* * * * *